United States Patent [19]

Goldfarb et al.

[11] Patent Number: 5,424,634
[45] Date of Patent: Jun. 13, 1995

[54] NON-DESTRUCTIVE FLEX TESTING METHOD AND MEANS

[75] Inventors: Samuel M. Goldfarb, Poughkeepsie; Paul R. Herb, LaGrangeville; Joseph M. Lukaitis, Pleasant Valley; Leathen Shi, Yorktown Heights, all of N.Y.

[73] Assignee: International Business Machines Corporation, Armonk, N.Y.

[21] Appl. No.: 199,042

[22] Filed: Feb. 18, 1994

[51] Int. Cl.⁶ ............................................. G01R 31/00
[52] U.S. Cl. ............................... 324/158.1; 73/812; 73/816; 73/838; 73/798; 73/432.1
[58] Field of Search ............... 324/158.1; 73/812, 816, 73/838, 798, 159, 432.1

[56] References Cited

U.S. PATENT DOCUMENTS

| | | | |
|---|---|---|---|
| 1,409,842 | 3/1922 | Foster . | |
| 2,340,733 | 2/1944 | Clark . | |
| 3,083,566 | 4/1963 | Huyser | 73/90 |
| 3,332,281 | 7/1967 | Spangler | 73/100 |
| 3,477,287 | 11/1969 | Dubach | 73/102 |
| 3,665,751 | 5/1972 | Paine et al. | 73/15.6 |
| 4,096,742 | 6/1978 | Musolf et al. | 73/94 |
| 4,170,141 | 10/1979 | Woo | 75/579 |
| 4,905,575 | 3/1990 | Knecht et al. | 92/103 |

Primary Examiner—Kenneth A. Wieder
Assistant Examiner—Kourosh Cyrus Khosravi
Attorney, Agent, or Firm—Bernard M. Goldman

[57] ABSTRACT

Describes a process for applying non-destructive cyclical mechanical stress to planar items in order to simulate the effects of cyclical thermal stresses. Latent defects are accelerated and screened early in a manufacturing process.

4 Claims, 3 Drawing Sheets

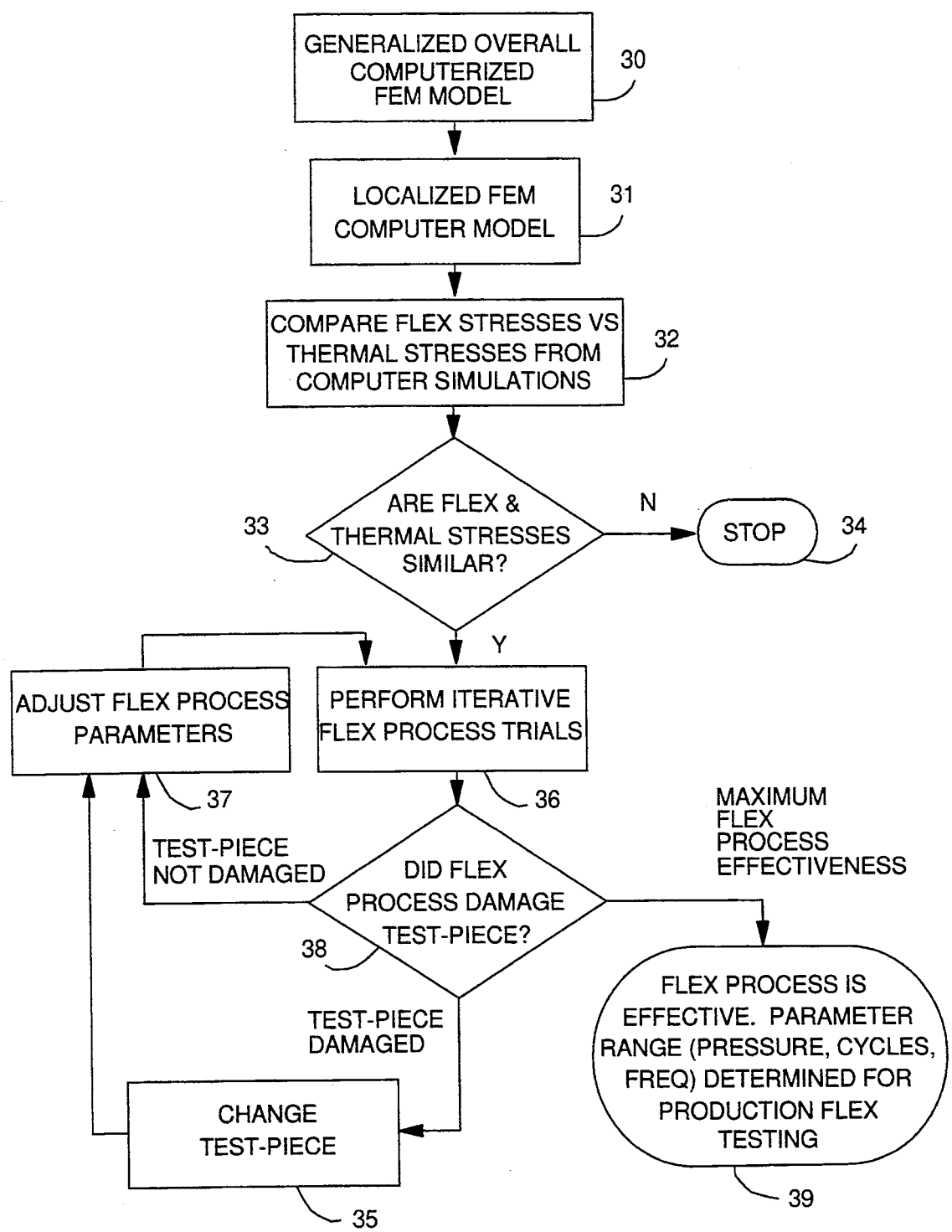

NON-DESTRUCTIVE FLEX TESTING METHOD AND MEANS

BACKGROUND OF THE INVENTION

This invention describes a process for applying non-destructive cyclical mechanical stress to planar items in order to simulate the effects of cyclical thermal stresses. A method for assessing and comparing thermal and mechanical stresses is also described, so that key process parameters (pressure, cycles) can be defined for any planar item. The objective of this invention is to accelerate latent defects, so that they can be screened early in the manufacturing process. This leads to higher reliability and lower costs.

Prior art describes other methods of simulating thermal stress with mechanical stress. However, those other methods cannot be used on delicate planar electronic components because they either contaminate the test piece or damage it with excessive contact force. This invention solves these shortcomings by not contaminating the test piece and not touching the test-piece's delicate top and bottom central regions.

SUMMARY OF THE INVENTION

This invention provides a new process for significantly reducing the likelihood of future failure of planar components by accelerating latent defects into solid defects. These solid defects can then be screened by subsequent functional testing.

The invention uses mechanical stressing to simulate the effect of thermal stress cycling in planar components. Mechanical stress cycles can be applied more quickly than thermal cycles because thermal cycling is limited by the heat capacity and thermal mass of the components.

Another objective of this invention is to provide a feasibility assessment methodology to determine if a component is amenable to this accelerated mechanical stress testing. The invention may perform mechanical stressing at a rate of 5 cycles per second as compared to 30–60 minutes per cycle for thermal testing. This example of the invention accelerates the testing process by a ratio of 15,000:1. This high ratio offers opportunities for quick and efficient testing in a production environment, as an alternative or supplement to cyclical thermal testing.

This invention uses a testing apparatus to simulate the thermal cycling process for a planar component by enabling it to be mechanically flexed bi-directionally by alternately applying controlled pressurized filtered-air. The component is alternately stressed in opposite directions in the apparatus for a predetermined number of cycles. In the apparatus, the air pressure builds up on one side of the planar component to a pre-determined maximum, while exhausting to the atmosphere on the other side. Then the other side is alternately pressurized to a pre-determined pressure, etc. Generally, the same maximum air pressure build-up is applied on the opposite sides of the component, but unequal maximum pressures may be advantageous in some situations.

An advantage of bi-directional flexing over unidirectional flexing of a planar component is that the former induces symmetric tensile and compressive bending stresses, maximizing the stress coverage within a planar component. This eliminates potential plastic distortion caused by cyclical stresses in the same direction.

The invention avoids use of hydraulic fluids and unfiltered pressurized air, since they contaminate components of the type to which the invention is directed.

Although the invention can be used both in development testing or in production testing of a planar component, the invention is primarily directed to the production testing of components. Thus, components with latent defects are forced by this invention to fail during production screening (before they are fabricated into higher-level assemblies). This production process can decrease costs associated with manufacturing products since failure after final assembly can be costly. Thus, this invention can decrease the overall cost of fabricated products by increasing their reliability and average life expectancy.

This invention requires proper adjustment of its critical parameters. Parameter adjustment is an involved process in the invention which requires the correct adjustment of its parameters. This is first done in a preliminary process herein called a "flexing feasibility assessment" procedure, which uses the following steps:

1. Perform a "generalized mechanical computer analysis" on the planar component to determine the peak stress level which occurs during simulated flexing of the component. This step may be supplemented using empirical testing. The purpose of this analysis is to correlate the air pressure in the fixture to the peak (yon Mises and principle) stresses in the planar component.

For example, flex testing a thin circular test piece causes it to deform into a curved shape, while inducing a tensile and compressive force gradient through the cross section. These forces, determined by the generalized analysis, can be used as inputs for the localized thermo-mechanical model.

2. Perform a "localized thermo-mechanical computer analysis" of the component (called herein the "test-piece") using the results of the general analysis as force or displacement input.

The first run of the localized model will use isothermal conditions with tensile and compressive force gradients applied to the cross section. The second run of the localized model will use temperature restraints representing cyclical thermal excursions, with no force inputs.

The purpose of the general and local analyses is to determine the internal forces generated while flexing a test-piece, and to use these forces as input into a thermo-mechanical model.

This step is preferably performed using commercially available stress analysis computer programs.

3. Compare the maximum mechanical stress values with the maximum thermal stresses in the thermo-mechanical model from step 2. If there is a correlation between the locations having maximum thermal stresses and the locations having maximum air-flex stresses, then flexing offers a good simulation of thermal cyclical stresses. Continue to step 4. If the correlation is poor, then this invention is not applicable.

4. An initial flex air pressure can be determined by working backwards from the actual working temperature range of the test-piece. Obtain the matching mechanical stress for a given temperature from the thermo-mechanical model. Determine the flexing air pressure which causes this mechanical stress from the generalized computer analysis. This analytic approach often needs to be verified and refined with empirical testing described in the next few steps.

5. Determine the number of flex cycles needed by estimating the number of thermal cycles expected in the life of the component.
6. Electrically pre-test circuits in a manufactured sample of the component to assure the sample is free of mature defects prior to actual flex testing.
7. Flex test the sample test-piece at the air pressure calculated in step 4 for the number of cycles estimated in step 5.
8. Electrically re-test the circuits in the component to determine if a failure occurred in the component due to the flex test.
9. If a component failure is found by step 8, replace the failed test-piece with a new sample component, reduce the air pressure in the apparatus by a small amount (e.g. 10 percent), and repeat steps 6 through 8 until no failure is found in the test-piece. Record the last-reduced air pressure.
10. If no component failure is found by step 8, increase the air pressure to the flexing apparatus in small increments. Repeat step 4 until the sample test-piece fails. The final flex air should be the highest pressure last used on a passing test-piece.
11. After the flex parameters of air pressure and number of cycles are determined, the flex process may be verified to assure that reliability and quality of the work-piece is not adversely affected by the flex stresses. Verification may be done by using thermal testing on a few samples of test-pieces which have successfully passed the production flex-stress test of step 10. Verification is successful if the samples do not fail during the thermal testing.

Proper adjustment of the air-pressure parameter is critical in the use of this invention. Excessive air pressure may create new defects (not previously existing) in a component. Inadequate air pressure may not affect latent defects and defeat the purpose of this invention.

The number of cycles per test simulates the life aging of the component and is the next most critical parameter. Hence, care is required in the operation of this invention to obtain its benefits.

SUMMARY OF THE DRAWINGS

FIG. 3 is a flow diagram of a flexing feasibility assessment process used to set up the operation of the invention in the apparatus shown in FIG. 1.

DETAILED DESCRIPTION OF THE PREFERRED EMBODIMENT

Figure 1:
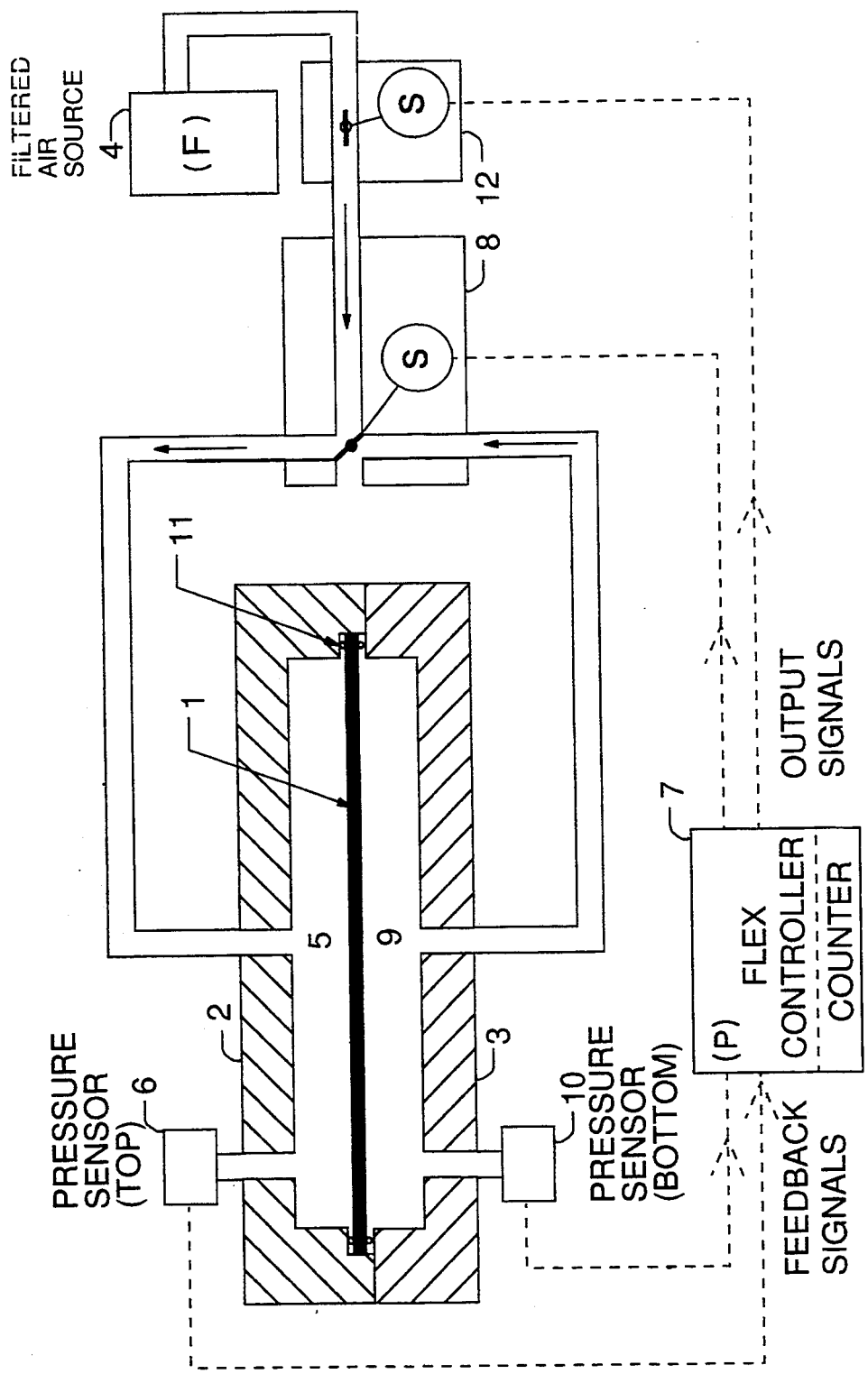
FIG. 1 shows flex apparatus used in the preferred embodiment of the invention.

FIG. 1 shows apparatus for holding and flexing a component (hereafter called a "test-piece") to which is being applied processes provided for a preferred embodiment of the invention. The test-piece is a planar component clamped into the apparatus. Examples of planar components include: computer circuit boards containing internally embedded electrical printed circuits, boards having tiny electrical circuits within and/or on one or both sides fabricated by VLSI (very large scale integration), silicon wafers having VLSI circuits, etc.

When such planar components are used in electrical products, they go through heating and cooling cycles as electricity is turned on and off for using the products. These thermal cycles cause stresses of varying magnitude to build up within parts of the planar components (boards, wafers, etc.). The deteriorating effects of the stress on printed circuit wires (lines) build up as the total number of cycles reaches the endurance limit, causing wires or other features to break. This is particularly so for latent defects, such as printed wires initially having sub-minimal strength, enabling the thermal stresses to eventually cause a break (failure) in such wires.

The purpose of this invention is to provide a flex testing process and apparatus for planar component to flush out existing failures, and to accelerate latent failures into permanent failures for enabling their detection before the planar component is fabricated into a product.

The apparatus shown in FIG. 1 has two mating sections 2 and 3, which are made of non-contaminating materials, regarding a test-piece contained therein. A planar component 1 is inserted between sections 2 and 3. Component 1 is called a test-piece, because it is to be stressed in the illustrated apparatus.

Test-piece 1 is placed between sections 2 and 3, between which it is mechanically clamped around its edges. A gasket 11 (which may be made of rubber) is cemented to each section 2 and 3, but is not cemented to test-piece 1 and freely contacts the edges of the test-piece. Gaskets 11 softly cushion test-piece 1 in the apparatus to avoid having any direct engagement between the edges of test-piece 1 and the mating sections 2 and 3, in order to prevent the test-piece from being stressed, scratched or damaged by mating sections 2 and 3. Gaskets 11 provide an air-tight seal on each side of the test-piece.

The shape of mating sections 2 and 3 conforms to the shape of the edge(s) of the test-piece. Therefore the clamping shape of sections 2 and 3, and of the test-piece edges, may be round, oval, square, rectangular, or any other shape; and gaskets 11 conform to that shape within the apparatus.

The opposite sections 2 and 3 are securely attached to each other by bolts, or other means. In a production environment, a pneumatic press may clamp sections 2 and 3 together (without clamping bolts) to allow fast insertion and removal of each test-piece from the apparatus by allowing it to be quickly opened and closed, while securely holding the test-piece in an air-tight manner between sections 2 and 3 with minimum stress induced in the test-piece.

An air tank 4 contains filtered pressurized air (with moisture removed) at a pressure (F). The pressurized air is alternately sent into opposite air chambers 5 and 9 separated by test-piece 1, which provides an air barrier between the chambers within the apparatus. Since contamination of the test-piece is often a major concern, clean dry filtered air must be used. Hydraulic fluids are not acceptable as an equivalent of air, because chemical interactions may occur causing damage to the test-pieces.

During operation of the apparatus, test-piece 1 is alternately bent in opposite directions as the pressurized air is alternately received into one of chambers 5 and 9, and exhausted from the other chamber. This alternate bending of the test-piece creates mechanical flexing stresses within the test-piece which simulates similar stresses that would be caused by thermal cycling of the test-piece after it is fabricated into a product. The maximum stresses induced in the test-piece are dependent on the pressure build up of the pressurized air received in chambers 5 and 9.

A solenoid 12 drives a valve which turns on and shuts off the pressurized air from source 4 to both chambers 5 and 9. Solenoid 12 operates under control of an electrical signal from a flex controller 7 to control the beginning and end of a flex test of the test-piece.

While air pressure is turned on by solenoid 12, another solenoid 8 allows only one of chambers 5 or 9 to receive pressurized air from source 4. When solenoid 8 positions its valve as illustrated in FIG. 1, chamber 5 receives the pressured air, and chamber 9 is exhausted to the atmosphere; so that work-piece 1 is flexed in a downward direction in FIG. 1. When solenoid 8 moves its valve to the opposite position, chamber 9 receives the pressurized air, and chamber 5 is exhausted to the atmosphere, so that work-piece 1 is flexed in a upward direction in FIG. 1. Solenoid 8 is signalled to alternately move its valve under control of controller 7 to cause the work-piece to be alternately flexed in opposite directions.

The maximum build up of air pressure in chambers 5 and 9 is respectively controlled by pressure sensors 6 and 10.

Each of these sensors outputs an electrical signal which varies with the air pressure currently within the respective chamber. When chamber 5 is receiving pressurized air, the air pressure gradually increases in chamber 5 to cause sensor 6 to send a signal of increasing amplitude (as a function of the pressure in chamber 6) to controller 7. When controller 7 senses that the signal has reached a predetermined pressure P, it generates and sends a signal to solenoid 8 to switch its valve to the other position in which chamber 5 exhausts to the atmosphere, and simultaneously applies pressurized air from source 4 to chamber 9. Sensor 10 in chamber 9 acts in the same manner to sense the air pressure therein and send a proportional signal to controller 7. When controller 7 determines that air pressure in chamber 9 has reached a predetermined pressure (P), it signals solenoid 8 to reverse its position to exhaust air from chamber 9 and guide pressurized air to chamber 5. Thus, controller 7 signals solenoid 8 to alternately pressurize the opposite chambers, which flexes the test-piece 1 in the apparatus.

The predetermined pressure settings (P) in controller 7 for the opposite chambers 5 and 9 are set to the same value in the preferred embodiment, but these pressure settings can be set to different pressures for special cases of testing.

Air pressure sensors, solenoids for operating air valves, and controllers for generating signals from predetermined signal levels provided by pressure sensors are well known in the commercial prior art, and therefore do not need to be described in further detail herein.

Also, the air pressure (F) in source 4 and the settings of pressures (P) in controller 7 controls the frequency of stressing of test-piece 1 in the apparatus. The higher the pressures (F), the higher the frequency of flexing, and vice-versa. This is because an increase in source pressure (F) increases the speed at which air is transmitted to chambers 5 and 9 to shorten the time of pressure build up within each chamber. And the lower the settings of pressures (P), the lower the frequency of flexing, and vice-versa.

Therefore both of the pressure settings (P) and (F) are regulated to control the frequency of stressing of test-piece 1. However, only pressure (P) controls the stress levels on the test-piece, which is considered the most important of the pressure parameters. Once pressure (P) is determined, the pressure (F) may be made as high as possible to maximize the speed of the flex test.

The duration of a flex test of test-piece 1 is controlled by an initial setting of a digital counter within controller 7. The initial setting of this digital counter is a "flex count", which determines the total number of flexes performed on the test-piece for a single test.

The count in counter 7 is incremented each time controller 7 sends a reversal signal (or a pair of reversal signals) to solenoid 8. When the current count reaches a predetermined set value, controller 7 sends a "stop signal" to solenoid 12 to stop the air flow from source 4 to the chambers. Solenoid 12 then closes its valve and thereby ends the current flex test of the test-piece. The flex test of test-piece 1 is then completed.

Figure 2:
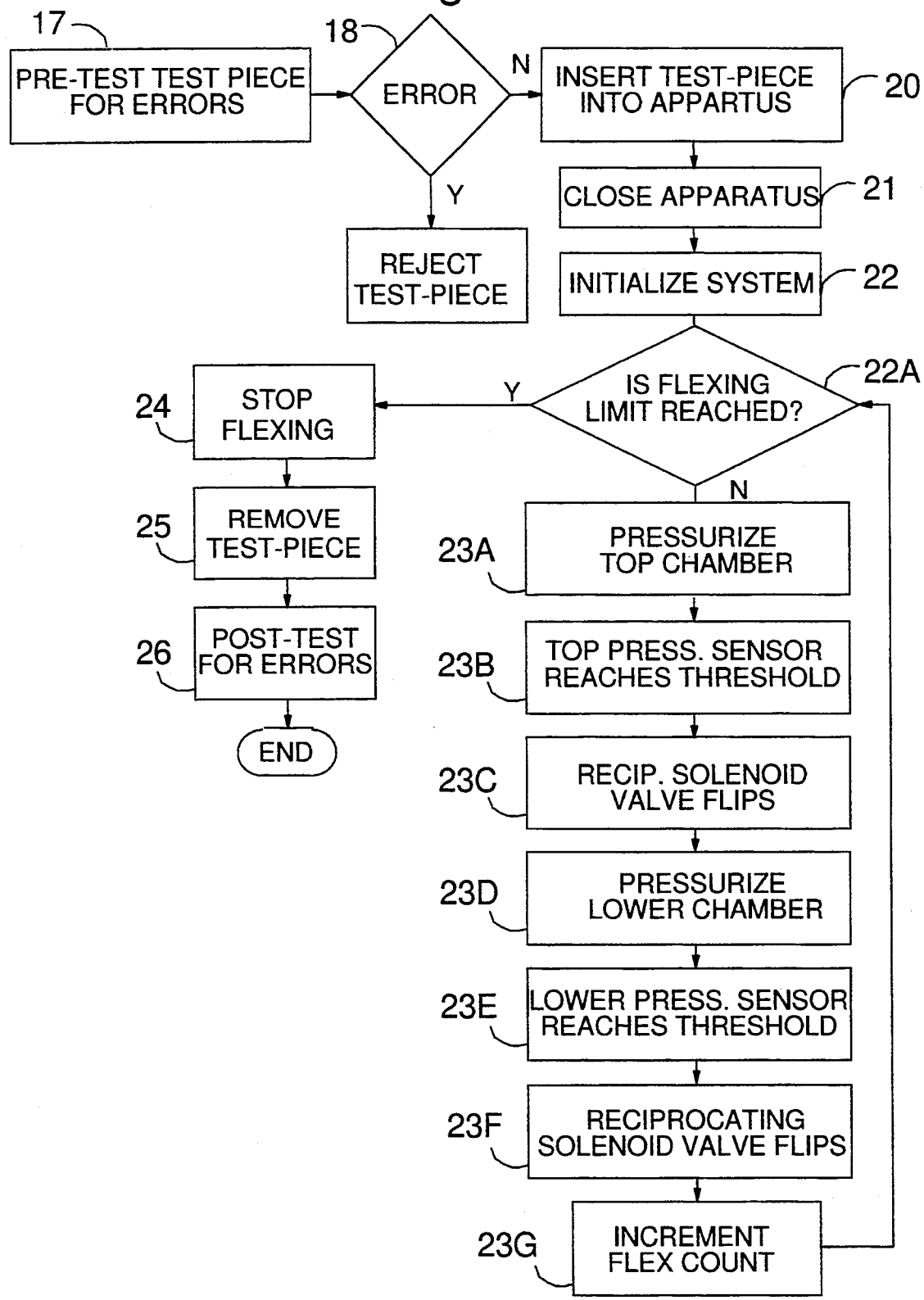
FIG. 2 is a flow diagram of a process used by the flex apparatus shown in FIG. 1.

FLEX TEST PROCESS:

FIG. 2 is a flow diagram of the flex process performed on a test-piece in the apparatus of FIG. 1. In step 17, a planar component, such as an electronic module substrate containing electronic semiconductor chips, is functionally tested to determine if it has any detectable error conditions which would cause its immediate rejection and prevent it from continuing as a test-piece. Inspection of the test-piece's surfaces is performed to assure that no scratches or cracks exist which might cause the test-piece to fracture prematurely during flexing. Any detectable error conditions in a test-piece are referred herein as matured errors. Upon the completion of the test in step 17, step 18 checks the result, If step 18 finds any mature error has been found by step 17, its "yes" path is taken to step 19 in which the test-piece is rejected, and it does not receive a flex test in the apparatus in FIG. 1.

Accordingly, if step 18 indicates no error condition has been found in the tests of step 17, the "no" path is taken to step 20 in which the test-piece is inserted into the apparatus of FIG. 1.

Step 21 represents the closing of the apparatus by moving sections 2 and 3 together to press their gaskets gently against the edges of the planar test-piece in an air-tight manner.

Step 22 represents initializing the system by checking the settings of pressure (F) in air source 4 to control the frequency of flex cycling during the test, checking the pressure settings of detection sensors 6 and 10 for the respective chambers 5 and 9 to control the stressing in the test-piece, and loading the flex count into the counter in controller 7.

The preferred embodiment uses a cycle rate of 5 cycles per second controlled by setting the air source pressure (F) to 40 pounds per square inch, and setting a flex count of 10,000 cycles in controller 7. Controller 7 is programmable so that any value of flex count may be entered as the flex count over a large range of values.

Then, step 22A begins the flexing by checking the setting of the counter in controller 7 for the limit value, where flexing of the test-piece is stopped.

Steps 23A–23G next occur and repeat until the flex cycle count is completed by step 22A finding the counter has incremented to 10,000, at which point step 22A takes its path to step 24 to stop the flexing operations.

In step 23A, controller 7 actuates solenoid 8 to its position shown in FIG. 1, which allows air to pressurize the top chamber 5 in FIG. 1. This flexes the test-piece 1 in the downward direction.

Step 23B indicates when the pressure in chamber 5 reaches its preset threshold (P) which is detected in controller 7 when the signal from sensor 6 reaches the predefined value. Upon reaching threshold (P), step 23C indicates a controller signal to solenoid 8 which flips its valve to its opposite position. Then step 23D represents the air pressurizing the opposite chamber 9 and exhausting the pressurized air from chamber 5. This flexes the test-piece 1 in the upward direction.

Step 23E indicates when the signal from sensor 10 reaches its predefined value in controller 7, at which time the controller sends a flip signal to solenoid 8 to reverse its valve position. Step 23F indicates when the solenoid 8 valve flips to pressurize chamber 5.

Step 23G then increments the counter in controller 7 for one cycle of flexing, and step 22A is again entered to repeat steps 23A-23G for each subsequent cycle of flexing, until step 22A finds the counter limit reached, in which case step 24 is entered to stop the flexing by having controller signal solenoid 12 to shut off the air flow from source 4 to the apparatus, and to signal solenoid 8 to move its valve to its neutral position which exhausts the air from both chambers 5 and 9.

Step 25 indicates the test-piece is removed from the apparatus at the end of the flex test.

Step 26 represents functional electrical tests which are done to circuits on the test-piece after the flex stressing is completed in the apparatus to determine if any failed circuit exists in the test-piece after the flex test, i.e. if any mature errors developed in the test-piece during the flexing. For electrical test-pieces such as silicon wafers, the error state of the test-piece circuits is verified by conventional test routines programmed for any logic and memory devices in the test-piece. If the test-piece is a multi-chip substrate, conductive path verification tests may be done on the circuits of the test-piece by using conventional multi-profile signal generators and detectors. Each of these post-flex tests is set to detect matured errors as low-level signal states indicating marginal or sub-acceptable performance by the test-piece that would lead to its premature failure.

FLEX FEASIBILITY ASSESSMENT:

Before the flex test is performed, an assessment process represented in FIG. 3 is used for determining the feasibility of using flex testing to simulate thermal testing. If feasibility is indicated by the assessment process, the parameters for a flex test (i.e. pressure, cycles, frequency) are defined at preliminary target stress levels indicated for a test-piece by computer analysis programs, and these parameters are used for an initial application of the flex test to a sample component of the type to be tested.

Feasibility and preliminary target stress levels are established by using commercially available structural analysis programs to model the internal stresses caused by flex testing in a component to be tested. These programs use the well-known Hooks Law, $F=KX$, and apply this relationship to any shaped geometry or material. These programs typically deal with Finite Element Methods (FEM). Examples of such commercially available programs are: CAEDS (Computer Aided Engineering Design System), ANSYS by Swanson Analysis Systems, Inc. located in Houston, Pa., and NASTRAN by MacNeal-Schwindler corporation in SanFernando, Calif.

The Finite Element Method (FEM) is a technique of applying Hooks law of material force versus deformation, defined by K, material stiffness. Stiffness is bulk material dependent and geometry dependent. For example, the axial stiffness of beam is $K=EA/L$, where E is modulus of elasticity, A is the cross sectional area, and L is the length. Combined, these 3 values define the beam stiffness. Any arbitrarily shaped part can be broken into many small building blocks or elements and by using (matrix) linear algebra, can be structurally simulated by numerous Hooks Law representations, which is done in the above cited commerically available computer programs. Elements can have different displacement assumptions, based upon stiffness characteristics such as linear or non-linear. The mathematics of FEM are centered upon equilibrium forces in a structure, that are represented by complex differential equations. Since the structure differential equations that represent force, stress and deflection are similar to those representing temperature, heat and thermal resistance, both phenomena can be represented by FEM and even applied simultaneously in the same analysis. The convenience of using commercial programs is that all the mathematics of matrix solutions and differential equation solutions are done transparently to the user of the programs. This invention combines the thermal and mechanical representations in determining how flex-mechanical stress relates to thermal induced stress.

In FIG. 3 step 30, generalized FEMs are created on a computer for representing the effects of mechanical stresses and of thermal stresses in a simulated test-piece undergoing flex conditions: uniform pressure loading across one face, and restraints along the outer perimeter on the opposite side. The generalized model determines the correlation between internal mechanical stresses and strains in the test-piece and flex air pressure. This analysis views the test-piece in a simplified manner, not accounting for minor internal features. Generalized assumptions are made about material properties. This model indicates whether or not the flex process is feasible by determining if high bending stresses result from reasonable air pressure and whether damaging forces are induced in the test-piece. Plus, internal forces generated by flexing are used as input into the "localized" FEM model. In step 31, a second more precise thermo-mechanical "localized" FEM model is created, incorporating the results of the previous generalized FEM model in the following way:

1. Use the internal forces from the general FEM model as input forces at the most critical or delicate regions in
   the localized FEM model. Determine the stresses in those critical features of the test piece induced by flex testing under isothermal conditions.

2. In a second run of the localized model, use temperature loading representing realistic thermal excursions, with no force input.

The localized model output represents mechanically induced stresses from flexing and thermal stresses due to a mismatch of material CTE's (coefficients of thermal expansion). For example, with an electronic wafer test-piece, the local FEM analysis focuses on stresses affecting microscopic conductive etched lines. And with substrate test-pieces, the local FEM analysis focuses on stresses affecting miniature internal electrical paths, since a breakage of either of them would cause operational failure of the test-piece.

COMPARING FLEX STRESSES VERSUS THERMAL STRESSES:

Step 32 in FIG. 3 compares the flex stresses and thermal stresses computed for the generalized model of step 30, and for the selected sub-parts in the localized models of step 31 for the test-piece.

If the computed results in step 32 indicate that flex stresses and thermal stresses have similar magnitudes in the same microscopic portions of the test-piece (step 33), then flex testing is feasible using the air pressure value (P) from the general FEM model of step 30. Step 36 is entered to perform flexing on the test-piece to begin a process for verifying the relationships between mechanical flexing and thermal cycling indicated in steps 30, 31 and 32.

If the results in step 32 show that flex stresses and thermal stresses are not similar in the same microscopic sub-parts of the test-piece, go to step 34 in FIG. 3 (stop). Flex testing is not appropriate for the test-piece.

Previous experience shows that the computer FEM model results are useful for initial assessments. However, it is essential to further verify the indicated relationship by actual physical testing of the planar component. This verification is done by using the flexing process described in FIG. 2 prior to production implementation of flex stressing the test-piece.

Step 36 applies the flex process described in FIG. 2. The number of flex cycles may be chosen by approximating the number of thermal cycles to occur over the expected lifetime of the test-piece. This is a good first estimate. Another approach is to accumulate enough flex cycles so that a significant percentage of the test-piece's endurance limit (10%) is used for screening defects. Experience shows that many more flex cycles may be needed to achieve equivalence between flexing and thermal cycling. The relatively high frequency of flexing makes this easy to accomplish.

After the flex testing is completed, step 38 in FIG. 3 is entered to evaluate the test-piece. Electrical tests on circuits determine if flexing caused latent defects to become solid defects. If solid defects are found, step 35 is entered. If no defects are found, step 37 is entered to determine how the parameters should be adjusted. If the test-piece piece was not damaged and the parameters used in the flex process appear optimum for production flex testing, step 39 is entered to start a final flex test of a real component to prove the parameter settings for use in production flex testing.

In step 36, flex testing trials are made with the best information obtained from the computer models. Target thermal stress levels for key microscopic features of the localized model are correlated to results of flex testing at a specific pressure (P). At this point, the key flex parameters, pressure and number of cycles are determined. Complex components, such as electronic chip wafers, may require in-depth material analyses and iterative flex experiments to assess potential damage from flexing to assure the component is not over-stressed.

If step 38 finds the component has sustained damage, the pressure and/or cycles are reduced and the component is replaced with a new one. Step 37 is entered to adjust the parameters for flex testing the new component in step 36.

If step 38 finds the flex testing is not effective and no defects were found in the flex-tested component, then the pressure and/or cycles are increased in step 37 to make it more effective. This iterative empirical investigation is needed because computer FEM models have limited ability to predict how cyclical loading can effect complex components.

When flex parameter determination is completed, and failure analysis indicates that the part was not over-stressed, then the flex parameters are considered established for production flex testing. Then, step 39 is entered to enable use of the defined parameters for flex testing of the component during production manufacturing.

It should be understood that the embodiments described herein have been provided by way of example and not by way of limitation. In light of the foregoing description, many modifications and variations which do not depart from the scope and spirit of the invention will occur to those of skill in the art. Thus, the scope of the invention is defined by the appended claims.

Having thus described our invention, what we claim as new and desire to secure by Letters Patent is:

1. A process for testing a planar electronic component for latent defects which will cause failure during the life of the component when the component is later used, comprising the steps of:

pre-testing the planar electronic component, as a test-piece, for detectable electrical errors in circuits in the test-piece;

placing the test-piece into an apparatus having chambers on opposite sides of the test-piece if the pre-testing step finds the test-piece has no detectable electrical errors;

applying pressurized filtered air to one chamber while exhausting air from the opposite chamber, and alternating this process with the chambers, to bi-directionally flex the test-piece up to a predetermined mechanical distortion at a predetermined frequency for a predetermined number of cycles, said predetermined mechanical distortion, frequency, and cycle parameters for the test piece having been determined by generalized computer stress analysis programs; and post-testing the test-piece for the existence of any detectable electrical error after the bi-directional flexing of the test-piece is completed to determine if any error condition developed in the test-piece during the bi-directional flexing.

2. A process for testing a planar component for latent defects as defined in claim 1, in which the applying step further comprises:

applying pressurized filtered air up to a predetermined pressure;

pressure sensing the air entering each chamber to detect when the predetermined pressure has been reached inside each chamber and stopping application of pressurized air to the chamber;

counting a predetermined number of cycles of alternation by the pressure sensing step;

ending the step of applying pressurized filtered air alternately to each chamber when the counting reaches the predetermined number of cycles; and wherein said post-testing the test-piece step includes testing for the existence of any out-of-tolerance electrical signals after the bi-directional flexing of the test-piece is ended to determine if any latent error condition in the test-piece is indicated.

3. A process for verifying parameters used in testing a planar electrical component for latent defects which can cause failure during the life of the component when the component is later used, comprising the steps of:

performing a computer analysis of mechanical stresses due to flexing a planar electrical component while held as a test-piece in a flexing apparatus based on overall geometry and structural parameters of the test-piece;

analyzing by a computer program of incremental mechanical stresses in incremental portions of structure in the test-piece based on coefficients of thermal expansion of materials used in construction of the test-piece over a temperature variation expected in use of the test-piece;

comparing and correlating the mechanical stresses in the test-piece obtained from the performing step and from the analyzing step for a multiplicity of thermal cycles expected over a life-time of the test-piece;

selecting a sample of the test-piece by pre-testing a sample and finding no detectable electrical error condition in electrical circuits of the sample;

flexing the sample for a number of test cycles related to the multiplicity of thermal cycles at a predetermined flexing frequency at a predetermined mechanical distortion of the sample to verify a correlation between flexing and thermal stressing for the test-piece indicated by the comparing and correlating step;

post-testing the sample to determine if the flexing step damaged the sample; and repeating the flexing step after replacing the sample of the test-piece if damaged by the afore-mentioned flexing step and changing the predetermined mechanical distortion for the flexing step.

4. A process for verifying parameters used in testing a planar electrical component for latent defects as defined in claim 3, the flexing step further comprising the substeps of:

placing the sample of the test-piece into an apparatus having chambers on opposite sides of the test-piece; and applying pressurized filtered air at a predetermined pressure to control a predetermined mechanical distortion of the test-piece in the chambers on opposite sides of said test piece to bi-directionally flex the test-piece for the predetermined flexing frequency.

* * * * *